United States Patent [19]
Andrianov et al.

[11] Patent Number: 6,015,563
[45] Date of Patent: Jan. 18, 2000

[54] POLYPHOSPHAZENE POLYELECTROLYTE IMMUNOADJUVANTS

[75] Inventors: Alexander K. Andrianov, Belmont; Lendon G. Payne, Arlington; Jonathan R. Sargent, Somerville; Sameer S. Sule, Woburn, all of Mass.

[73] Assignee: AVANT Immunotherapeutics, Inc., Needham, Mass.

[21] Appl. No.: 09/185,834

[22] Filed: Nov. 4, 1998

Related U.S. Application Data

[62] Division of application No. 08/478,552, Jun. 7, 1995.
[51] Int. Cl.$^7$ .......................... A61K 39/00; A61K 45/00; A61K 51/00
[52] U.S. Cl. ...................................... 424/184.1; 424/280.1; 424/1.11; 514/110; 514/114; 514/75; 514/137
[58] Field of Search .......................... 424/184.1, 280.1, 424/1.11; 514/110, 114, 75, 137

[56] References Cited

U.S. PATENT DOCUMENTS

| | | | |
|---|---|---|---|
| 5,284,934 | 2/1994 | Allen, Jr. | 530/370 |
| 5,494,673 | 2/1996 | Adrianov et al. | 424/280.1 |
| 5,855,895 | 1/1999 | Andrianov et al. | 424/184.1 |

FOREIGN PATENT DOCUMENTS

WO 94/09822  5/1994  WIPO.

OTHER PUBLICATIONS

Cohen, et al., *J. Am. Chem. Soc.*, vol. 112, pp. 7832–7833 (1990).

Andrianov, et al., *J. Controlled Release*, vol. 27, pp. 69–77 (1993).

*Primary Examiner*—Louise N. Leary
*Attorney, Agent, or Firm*—Elliot M. Olstein; Raymond J. Lillie

[57] ABSTRACT

A polyphosphazene polyelectrolyte immunoadjuvant having improved water solubility, a vaccine composition of the immunoadjuvant and an antigen or immunogen and methods of their use in producing or enhancing an immunoprotective response in a host are disclosed.

22 Claims, No Drawings

POLYPHOSPHAZENE POLYELECTROLYTE IMMUNOADJUVANTS

This is a Divisional of application Ser. No. 08/478,522 filed Jun. 7, 1995.

This application relates to the field of polymers for biomedical applications, and in particular describes polymers that are useful as immunoadjuvants.

A wide variety of antigens stimulate the production of antibodies in animals and confer protection against subsequent infection. However, some antigens are unable to stimulate an effective immune response.

The immunogenicity of a relatively weak antigen is often enhanced by the simultaneous administration of the antigen with an adjuvant, a substance that is not immunogenic when administered alone, but will induce a state of mucosal and/or systemic immunity when combined with the antigen. It has been traditionally thought that adjuvants, such as mineral oil emulsions or aluminum hydroxide, form an antigen depot at the site of injection that slowly releases antigen. Recent studies by Allison and Byars, in: "Vaccines: New Approaches to Immunological Problems:, R. W. Ellis, ed., p. 431, Butterworth-Heinemann, Oxford (1992) indicate that adjuvants enhance the immune response by stimulating specific and sometimes very narrow branches of the immune response by the release of cytokines. Unfortunately, many immunoadjuvants, such as Freund's Complete Adjuvant, are toxic and are therefore only useful for animal research purposes, not human vaccinations. Freund's Complete Adjuvant contains a suspension of heat-killed Mycobacterium tuberculosis in mineral oil containing a surfactant and causes granulomatous lesions in animals at the site of immunization. Freund's adjuvant may also cause the recipient of a vaccine to test positive for tuberculosis.

Some synthetic polyelectrolytes have been found to provide immunostimulation when combined with an antigen. For example, the adjuvant activity of polyacrylic acid (PAA), copolymers of acrylic acid and N-vinylpyrrolidone (CP-AAVPD), poly-2-methyl-5-vinyl pyridine (PMVP), poly-4-vinylN-ethylpyridinium bromide (PVP-R$_2$) and similar compounds, when conjugated to an antigen, has been studied by Petrov et al., Jhurnal Vses. Khim. Ob-va im. D. I. Mendeleeva, 33:22–42 (1988). The immunomodulatory effect of polyelectrolyte complexes containing many of these same polyelectrolytes has also been more recently reviewed by Petrov et al., Sov. Med. Rev. D. Immunol., 4:1–113 (1992). However, the toxicity and biodegradability of these polymers has not been studied and may prevent use of these polymers as adjuvants for use in humans.

A non-toxic adjuvant or carrier having the ability to stimulate an immune response to non-antigenic or weakly antigenic molecules would fill a long-sought need in the development and administration of vaccines.

The present invention provides an adjuvant that can be safely administered to humans and animals with minimal toxicity, is biodegradable and which has the additional advantage of being highly water soluble. The present invention also provides a rapid and efficient method of synthesizing a polymer, such as polyphosphazene, for use as an adjuvant.

Thus, in one aspect, the present invention provides a polyphosphazene polyelectrolyte wherein at least a portion of said polyphosphazene polyelectrolyte has the formula:

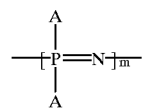

wherein each A is independently selected from X or Y in which (1) X is

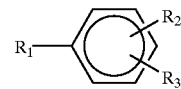

in which R$_1$ is —N(R$_4$)—, —O— or —OR$_5$— where R$_4$ is hydrogen or a C$_1$–C$_4$ alkyl(preferably hydrogen) and R$_5$ is a C$_1$–C$_3$ alkylene(preferably methylene) moiety, R$_2$ is at least one carboxylic acid moiety which can be attached at any ring position directly or through an alkylene, preferably a methylene and R$_3$ is hydrogen or another substituent moiety such as an alkoxy, for example a methoxy moiety;
(2) Y is selected from the group consisting of
  (a) (OCH$_2$CH$_2$)$_n$OR$_6$ in which n is 1 to 120 and R$_6$ is a C$_1$ to C$_{10}$ hydrocarbon, e.g. an aliphatic saturated or unsaturated hydrocarbon (preferably a C$_1$ to C$_3$ aliphatic hydrocarbon) or an aromatic hydrocarbon(including alkyl substituted aromatic hydrocarbons); and
  (b) (B)OR$_7$ in which B is a polyoxypropylene/polyoxyethylene block copolymer and R$_7$ is a C$_1$ to C$_{10}$ hydrocarbon, an aliphatic saturated or unsaturated hydrocarbon or an aromatic hydrocarbon, including alkyl substituted aromatic hydrocarbons;
(3) X and Y are in a range of ratios of 1:40 to 40:1; and
(4) m is 3 to 100,000.

The phosphazene is a polyelectrolyte that is biodegradable and exhibits minimal toxicity when administered to animals, such as humans. It is ideal for use as an immunoadjuvant. Two examples of polyphosphazenes that are particularly preferred as immunoadjuvants are poly[p-(carboxylatophenoxy) (methoxyethoxy) phosphazenen] and poly[p-(carboxylatophenoxy) (methoxyethoxyethoxy) phosphazene]. When cross-linked with a multivalent ion, the polymer becomes less soluble, resulting in slower release of the polymer from the site of administrantion.

In another aspect the invention provides a composition comprising the polyphosphazene polyelectrolyte of the invention in combination with an antigen or immunogen in the form of a vaccine.

In another aspect the invention provides a method of inducing or enhancing an immunoprotective response to an immunological challenge in a host which comprises administering to said host an immunogen capable of sensitizing said host to said immunological challenge and a polyphosphazene polyelectrolyte immunoadjuvant of the invention. The immunogen and adjuvant can be administered separately or as a composition.

A vaccine composition is prepared by either mixing or conjugating the polymer adjuvant with an antigen prior to administration. Alternatively, the polymer and antigen can be administered separately to the same site.

The term "pharmaceutically acceptable cation" refers to an organic or inorganic moiety that carries a positive charge and that can be administered as a counteraction in a phosphazene polyelectrolyte.

The polymeric adjuvant of the invention is a polyphosphazene that is soluble in water at physiological pH.

Polyphosphazenes are polymers with backbones consisting of alternating phosphorus and nitrogen, separated by alternating single and double bonds. Each phosphorous atom is covalently bonded to two pendant groups ("A"). The repeat unit in the polyphosphazenes of this invention has the following formula:

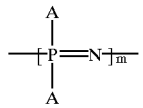

wherein each A is independently selected from X or Y as described above.

In general, when the polyphosphazene has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

A preferred phosphazene polyelectrolyte immunoadjuvant contains pendant groups that include carboxylic acid moieties. While the acidic groups are usually on nonhydrolyzable pendant groups, they can alternatively, or in combination, also be positioned on hydrolyzable groups.

Most preferably the polymer is a polyphosphazene that includes pendant groups that include carboxylic acid moieties on pendant groups that do not hydrolyze under the conditions of use.

In one preferred embodiment, X is selected from the group consisting of:

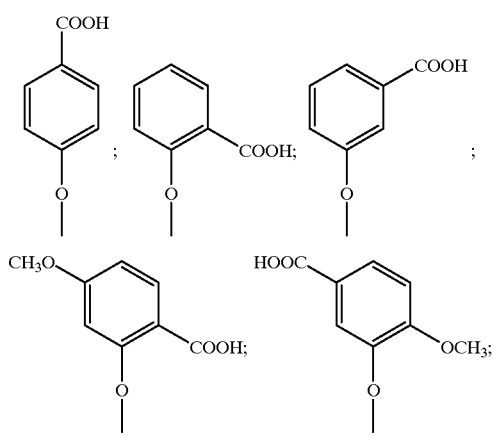

-continued

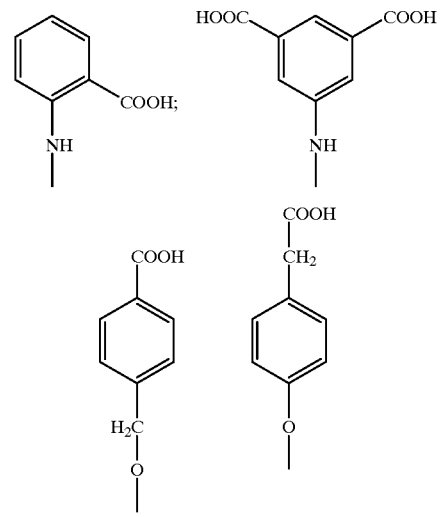

In another aspect the invention provides a polyphosphazene having the formula:

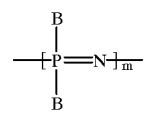

wherein m is 3 to 100,000 and each B is

Ortho-O—C$_6$H$_4$COOH

This polyphosphazene is also suitable for use as an immunoadjuvant in accordance with the invention.

The phosphazene polyelectrolytes of the invention contain ionized or ionizable pendant groups that render the polyphosphazene anionic, cationic or amphiphilic. The ionic groups can be in the form of a salt, or, alternatively, an acid or base that is or can be at least partially dissociated. Any pharmaceutically acceptable monovalent cation can be used as counterion of the salt, including but not limited to sodium, potassium, and ammonium. The phosphazene polyelectrolytes can also contain non-ionic side groups. The phosphazene polyelectrolyte can be biodegradable or nonbiodegradable under the conditions of use. The ionized or ionizable pendant groups are preferably not susceptible to hydrolysis under the conditions of use.

The phosphazene polyelectrolyte is preferably biodegradable to prevent eventual deposition and accumulation of polymer molecules at distant sites in the body, such as the spleen. The term biodegradable, as used herein, means a polymer that degrades within a period that is acceptable in the desired application, typically less than about five years and most preferably less than about one year, once exposed to a physiological solution of pH 6–8 at a temperature of approximately 25° C.–37° C.

Crosslinked polyphosphazenes for use as immunoadjuvants can be prepared by combining a phosphazene polyelectrolyte with a metal multivalent cation such as zinc, calcium, bismuth, barium, magnesium, aluminum, copper, cobalt, nickel, or cadmium.

Polyphosphazenes, including phosphazene polyelectrolytes, can be prepared by a macromolecular nucleophilic substitution reaction of poly(dichloro phosphazene) with a wide range of chemical reagents or mixture of reagents in accordance with methods known to those skilled in the art. Preferably, the phosphazene polyelectrolytes are made by reacting the poly(dichloro phosphazene) with an appropriate nucleophile or nucleophiles that displace chlorine. Desired proportions of hydrolyzable to non-hydrolyzable side chains in the polymer can be obtained by adjusting the quantity of the corresponding nucleophiles that are reacted with poly (dichlorophosphazene) and the reaction conditions as necessary. Preferred polyphosphazenes for immunoadjuvant activity have a molecular weight of over 1,000.

In another embodiment, the polyphosphazene polymer adjuvant of the invention is employed in a composition to induce an immunogenic response, in particular, a protective response when the composition is parenterally or orally administered to a patient.

The antigen with which the adjuvants of the invention are used can be derived from a cell, bacteria or virus particle or portion thereof. The antigen can be a protein, peptide, polysaccharide, glycoprotein, glycolipid, nucleic acid or combination thereof which elicits an immunogenic response in an animal, for example, a mammal, bird, or fish. The immunogenic response can be humoral or cell mediated. In the event the material to which the immunogenic response is to be directed is poorly antigenic, it may be conjugated to a carrier such as albumin or to a hapten, using standard covalent binding techniques, for example, with one of the several commercially available reagent kits.

In one embodiment, the polymer is used to deliver nucleic acid which encodes antigen to a mucosal surface where the nucleic acid is expressed. In such a case, the polymer is in the form of a hydrogel (crosslinked) and is in particulate form.

Examples of preferred antigens include viral proteins such as influenza proteins, human immunodeficiency virus (HIV) proteins and hepatitis B proteins, and bacterial proteins and lipopolysaccharides such as gram negative bacterial cell walls and *Neisseria gonorrhea* proteins.

An immunogenic composition, or vaccine, is prepared by combining the polymer adjuvant with an antigen. Approximately 0.5–0.0001 parts of antigen is added to one part polymer, preferably by stirring a solution of polymer and antigen until a solution or suspension is obtained, preferably for 10 minutes or more at 25° C. The polymer is preferably combined with the antigen using a method dispersing the antigen uniformly throughout the adjuvant. Methods for liquefying the polymer include dissolving the polymer in an aqueous-based solvent, preferably having a pH range of between 7.1 and 7.7, and melting the polymer. The latter is useful only when the antigen is stable at the polymer melting temperature. The antigen is then mixed with the polymer. The polymer and the antigen, in solid form, for example, when the antigen is lyophilized, can also be physically mixed together, for example, by compression molding. The polymer can also be used to encapsulate the antigen, for example, using the method of U.S. Pat. No. 5,149,543 to Cohen, et al., the teachings of which are incorporate herein, or by spray drying a solution of polymer and antigen.

Alternatively, microspheres containing the antigen and adjuvant can be prepared by simply mixing the components in an aqueous solution, and then coagulating the polymer together with the substance by mechanical forces to form a microparticle. The microparticle can be stabilized, if necessary or desired, using electrolytes, pH changes, organic solvents, heat or frost to form polymer matrices encapsulating biological material.

The polymer of the present invention is soluble in physiologically buffered saline (PBS).

The polymer can also be covalently conjugated with the antigen to create a water-soluble conjugate in accordance with methods well-known to those skilled in the art, usually by covalent linkage between an amino or carboxyl group on the antigen and one of the ionizable side groups on the polymer.

In an alternative preferred embodiment, the polymer is cross-linked with a multivalent ion, preferably using an aqueous solution containing multivalent ions of the opposite charge to those of the charged side groups of the polyphosphazene, such as multivalent cations if the polymer has acidic side groups or multivalent anions if the polymer has basic side groups.

Preferably, the polymers are cross-linked by di and trivalent metal ions such as calcium, copper, aluminum, magnesium, strontium, barium, tin, zinc, and iron, organic cations such as poly(amino acid)s, or other polymers such as poly(ethyleneimine), poly(vinylamine) and polysaccharides.

It will be understood by those skilled in the art that the immunogenic vaccine composition can contain other physiologically acceptable ingredients such as water, saline or a mineral oil such as Drakeol™, Markol™, and squalene, to form an emulsion.

The immunogenic composition can be administered as a vaccine by any method known to those skilled in the art that elicits an immune response, including parenterally, orally, or by transmembrane or transmucosal administration. Preferably, the vaccine is administered parenterally (intravenously, intramuscularly, subcutaneously, intraperitoneally, etc.), and preferably subcutaneously. Non-limiting examples of routes of delivery to mucosal surfaces are intranasal (or generally, the nasal associated lymphoid tissue), respiratory, vaginal and rectal.

The dosage is determined by the antigen loading and by standard techniques for determining dosage and schedules for administration for each antigen, based on titer of antibody elicited by the polymer-antigen administration, as demonstrated by the following examples.

Although in the preferred embodiment the polymer antigen mixture is administered simultaneously, in an alternative embodiment, the polymer and antigen are administered separately to the same or nearby site. The polymer serves to attract cells of the immune system to the site, where they process the antigen.

The polyphosphazene adjuvants and methods of synthesis will be further understood by reference to the following non-limiting examples.

EXAMPLE 1

Preparation of $[NP(OC_2H_4OCH_3)_{0.18}(OC_6H_4COOH)_{1.82}]$

Under nitrogen, in a 500 ml Erlenmeyer flask 0.39 grams of NaH was suspended in 82 ml of anhydrous tetrahydrofuran (hereinafter THF). To this suspension 2 ml of freshly distilled 2-methoxyethanol was added dropwise, resulting in a vigorous reaction. The clear solution which resulted, was added slowly to a 500 ml three neck flask which contained 100 ml of a 3% poly[di(chloro)phosphazene] solution in THF. After 2 hours of reflux, a solution of 48 grams NaO($C_6H_4$)COO$C_3H_7$ in 180 ml of THF, which was prepared via a reaction of NaH and excess HO($C_6H_4$) COO$C_3H_7$ in THF, was added to the polymer mixture. The solution was refluxed for an additional 24 hours.

The polymer solution in THF was precipitated in hexanes, redissolved in THF and then precipitated in ethanol. The polymer was then redissolved a final time in THF, precipitated in water and then vacuum dried.

A 250 ml glass media bottle was charged with 150 ml of THF stabilized with BHT (hereinafter THF), and 1.5 gram of a co-polymer containing 0.9% of —O($C_6H_4$)COO$C_3H_7$ groups. A magnetic stirbar was added and the sample was allowed to dissolve overnight while being agitated.

A 500 ml three neck flask was charged with 15 grams of potassium tert-butoxide (Aldrich) and 150 ml of THF. A magnetic stirbar was added and the potassium tert-butoxide was dissolved in the THF. To this solution 5 ml of water followed by the polymer solution, described above, was slowly added. The vessel was capped and allowed to mix at room temperature for 72 hours.

The solution was transferred to a one neck round bottom flask, with 150 ml of water. The THF was removed under vacuum and the solution was acidified using HCl causing the precipitation of the polymer. The polymer was collected by filtration, redissolved in NaOH, pH balanced to 8–9 pH using dilute HCl and purified on a G-10 column using a running buffer of ammonium bicarbonate. The polymer was lyophilized and stored under refrigeration.

The structure was confirmed by NMR. $^{31}$P-NMR showed two peaks (−12.5 ppm and −18.3 ppm) corresponding to the mixed and homosubstituted phosphorous respectively. $^1$H-NMR showed four peaks at 7.3 ppm, 6.51 ppm, 3.29 ppm, and 2.61 ppm. The first two correspond to the four aromatic protons on the (O$C_6H_4$COOH) side groups and the final two correspond to aliphatic protons on the (O$C_2H_4$COO$H_3$) side groups. The structure was quantitated using the hydrogen NMR.

The polymer was found to be soluble in aqueous base and PBS (pH 7.4). The polymer swelled in water, and was not soluble in THF and ethanol.

EXAMPLE 2

Preparation of [NP(O$C_2H_4$O$CH_3$)$_{0.47}$ (O$C_6H_4$COOH)$_{1.53}$]

Under nitrogen, in a 500 ml Erlenmeyer flask 0.77 grams of NaH was suspended in 79 ml of THF. To this suspension 3 ml of freshly distilled 2-methoxyethanol was added dropwise, resulting in a vigorous reaction. The clear solution which resulted, was added slowly to a 500 ml three neck flask which contained 100 ml of a 3% poly[di(chloro) phosphazene] solution in THF. After 2 hours of reflux, a solution of 45 grams NaO($C_6H_4$)COO$C_3H_7$ in 170 ml of THF, which was added to the polymer mixture. The solution was refluxed for an additional 24 hours.

The polymer solution in THF was precipitated in hexanes, redissolved in THF and then precipitated in 70% ethanol acidified with HCl. The polymer was then vacuum dried.

The propyl ester was converted to the acid form, and purified using the deprotection scheme described in Example 1.

The structure was confirmed by NMR. $^{31}$P-NMR showed three peaks at −6.4 ppm, −12.5 ppm and −18.3 ppm corresponding to the mixed and homosubstituted phosphorous respectively. $^1$H-NMR showed four peaks at 7.4 ppm, 6.6 ppm, 3.7 ppm, and 2.7 ppm. The first two correspond to the four aromatic protons on the (O$C_6H_4$COOCH) side groups, and the final two correspond to aliphatic protons on the (O$C_6H_4$OCOO$CH_3$) side groups. The structure was quantitated using the hydrogen NMR.

The polymer was found to be soluble in aqueous base, PBS (pH 7.4) and water. The polymer was not soluble in THF and ethanol.

The polymer was characterized by GPC with multi angled laser light scattering (hereinafter MALLS). The number average molecular weight (hereinafter Mn) was found to be 208 kDa. The weight average molecular weight (hereinafter Mw) was found to be 435 kDa. The change in refractive index over the change in concentration (hereinafter dn/dc) was found to be 0.249 ml/gram.

EXAMPLE 3

Preparation of [NP(O$C_2H_4$O$CH_3$)$_{0.42}$ (O$C_6H_4$COOH$_{1.58}$]

Under nitrogen, in a 500 ml Erlenmeyer flask 1.15 grams of NaH was suspended in 75 ml of THF. To this suspension 4 ml of freshly distilled 2-methoxyethanol was added dropwise, resulting in a vigorous reaction. The clear solution which resulted was added slowly to a 500 ml three neck flask which contained 100 ml of a 3% poly[di(chloro) phosphazene] solution in THF. After 2 hours of reflux, a solution of 48 grams NaO($C_6H_4$)COO$C_3H_7$ in 180 ml of THF, which was prepared via a reaction of NaH and excess HO($C_6H_4$)COO$C_3H_7$ in THF, was added to the polymer mixture. The solution was refluxed for an additional 24 hours.

The polymer solution in THF was precipitated in hexanes, redissolved in THF and then precipitated in 60% ethanol acidified with HCl. The polymer was then redissolved a final time in THF, precipitated in water and then vacuum dried.

The propyl ester was converted to the acid form and purified using the deprotection scheme described in Example 1, with the exception of using heat to help in the precipitation of polymer after the addition of the acid.

The structure was confirmed by NMR. $^{31}$P-NMR showed three peaks at −5 ppm, −12.5 ppm and −17.9 ppm corresponding to the mixed and homosubstituted phosphorous respectively. $^1$H-NMR showed four peaks at 7.4 ppm, 6.6 ppm, 3.6 ppm and 2.8 ppm. The first two correspond to the four aromatic protons on the (O$C_6H_4$)COO$C_3H_7$ and the final two correspond to aliphatic protons on the (O$C_2H_4$CO$C_3$) side groups. The structure was quantitated using the hydrogen NMR.

The polymer was found to be soluble in aqueous base, PBS (pH 7.4), and water. The polymer was not soluble in THF and ethanol.

The polymer was characterized by GPC with MALLS. The Mn, Mw, and dn/dc were found to be 497 kDa, 857 kDa, 0.166 ml/gram.

EXAMPLE 4

Preparation of [NP(O$C_2H_4$O$C_2H_4$O$CH_3$)$_{0.38}$ (O$C_6H_4$COOH)$_{1.62}$]

Under nitrogen, in a 500 ml Erlenmeyer flask 0.39 grams of NaH was suspended in 84 ml of anhydrous THF. To this suspension 2 ml of freshly distilled 2, (2-methoxyethoxy)

ethanol was added dropwise, resulting in a vigorous reaction. The clear solution which resulted, was added slowly to a 500 ml three neck flask which contained 100 ml of a 2% poly[di(chloro)phosphazene] solution in THF. After 2 hours of reflux, a solution of 48 grams $NaO(C_6H_4)COOC_3H_7$ in 180 ml of THF, which was prepared via a reaction of NaH and excess $HO(C_6H_4)$ $COOC_3H_7$ in THF, was added to the polymer mixture. The solution was refluxed for an additional 24 hours.

The polymer solution in THF was precipitated in hexanes, redissolved in THF and then precipitated in 50% ethanol acidified with HCl. The polymer was then redissolved a final time in THF, precipitated in water and then vacuum dried.

The propyl ester was converted to the acid form and purified using the deprotection scheme described in Example 1.

The structure was confirmed by NMR. $^{31}$P-NMR showed three peaks at −6.0 ppm, −12.5 ppm, −18.25 ppm corresponding to the mixed and homosubstituted phosphorous, respectively. $^1$H-NMR showed four peaks at 7.3 ppm, 6.5 ppm, 3.4 ppm, and 2.8 ppm. The first two correspond to the four aromatic protons on the $(OC_6H_4COOH)$ side groups and the final two correspond to aliphatic protons on the $((OC_2H_4)_2OCH_3)$ side groups. The structure was quantitated using the hydrogen NMR.

The polymer was found to be soluble in aqueous base, PBS (pH 7.4). the polymer swelled in water, and was not soluble in THF and ethanol.

The polymer was characterized by GPC with MALLS. The Mn, Mw, and dn/dc were found to be 194 kDa, 373 kDa and 0.262 ml/gram.

EXAMPLE 5

Preparation of $[NP(OC_2H_4OC_2H_4OCH_3)_{0.80}$ $(OC_6H_4COOH)_{1.21}]$

Under nitrogen, in a 500 ml Erlenmeyer flask 0.77 grams of NaH was suspended in 71 ml of anhydrous THF. To this suspension 3 ml of freshly distilled 2,(2-methoxyethoxy) ethanol was added dropwise, resulting in a vigorous reaction. The clear solution which resulted, was added slowly to a 500 ml three neck flask which contained 100 ml of a 3% poly[di(chloro)phosphazene] solution in THF. After 2 hours of reflux, a solution of 45 grams $NaO(C_6H_4)COOH_3H_7$ in 170 ml of THF, which was prepared via a reaction of NaH and excess $HO(C_6H_4)COOH_3H_7$ in THF, was added to the polymer mixture. The solution was refluxed for an additional 24 hours.

The polymer solution in THF was precipitated in hexanes, re-dissolved in THF and then precipitated in 10% ethanol acidified with HCl. The polymer was then vacuum dried. Polymer contains a lot of $p-HO(C_6H_4)COOC_3H_7$.

The propyl ester was converted to the acid form, and purified using the deprotection scheme described in Example 1.

The structure was confirmed by NMR. $^{31}$P-NMR showed three peaks at −6.6 ppm, −12.36 ppm and −18.32 ppm corresponding to the mixed and homosubstituted phosphorous respectively. $^1$H-NMR showed four peaks at 7.5 ppm, 6.8 ppm, 3.5 ppm, and 3.0 ppm. The first two correspond to the four aromatic protons on the $(OC_6H_4COOH)$ side groups and the final two correspond to aliphatic protons on the $((OC_2H_4)_2OCH_3)$ side groups. The structure was quantitated using the hydrogen NMR.

The polymer was found to be soluble in aqueous base, PBS (pH 7.4) and water. The polymer was not soluble in THF and ethanol.

The polymer was characterized by GPC with MALLS. The Mn, Mw, and the dn/dc were found to be 320 kDa, 551 kDa, 0.163 ml/gram.

EXAMPLE 6

Preparation of $[NP((OC_2H_4)_nOCH_3)_{0.16}$ $(OC_6H_4COOH_{1.84}]$

Under nitrogen, in a 500 ml bottle 0.15 grams of NaH was suspended in 100 ml of anhydrous THF. To this suspension 5.8 grams of freshly distilled 750 mw polyethyleneglycol was added. The bottle was sealed, and vented several times over 72 hours to let off hydrogen gas. The clear solution which resulted was added slowly to a 500 ml three neck flask which contained 109 ml of a 2% poly[di(chloro) phosphazene] solution in THF. After 2 hours of reflux, a solution of 50 grams $NaO(C_6H_4)COOC_3H_7$ in 190 ml of THF, which was prepared via reaction of NaH and excess $HO(C_6H_4)COOC_3H_7$ in THF, was added to the polymer mixture. The solution was refluxed for an additional 24 hours. The polymer solution in THF was precipitated in hexanes, and then vacuum dried.

The propyl ester was converted to the acid form, and purified using the deprotection scheme described in Example 1.

The structure was confirmed by NMR. $^1$H-NMR showed four peaks at 7.2 ppm, 6.4 ppm, 3.5 ppm, and 3.2 ppm. The first two correspond to the four aromatic protons on the $(OC_6H_4COOH)$ side groups, and the final two correspond to aliphatic protons on the $((OC_2H_4)_nOCH_3)$ side groups, where n is such that the average molecular weight is 750, i.e. n averages 16.3. The structure was quantitated using the hydrogen NMR.

The polymer was found to be soluble in aqueous base, PBS (pH 7.4), and water. The polymer swelled in ethanol and was not soluble in THF.

EXAMPLE 7

Preparation of $[NP(Ortho-OC_6H_4COOH)_2]$

Ethyl salicylate (36.25 g, 0.22 mol) was dissolved in 87 ml of THF. This was added to a suspension of NaH (4.36 g, 0.11 mol) in 65.5 ml of THF. The resulting solution was added to a solution of the polydichlorophosphazene (2.07 g, 0.02 mol) in 104 ml of THF. The reaction mixture was stirred at reflux for 80 hours, stripped to ⅓ volume and poured into 800 ml of heptane. The precipitated polymer was further purified by redissolving in 800 ml of ethanol followed by precipitation in 2000 ml of water. The substituted polymer was isolated via filtration and vacuum drying. $^1$H NMR showed polymer peaks at 7.2 ppm and 6.5 ppm due to the aromatic protons and at 3.7 ppm and 1.0 ppm due to the aliphatic ester protons. The $^{31}$p NMR showed the polymer peak at −33.02 ppm.

The dried polymer sample (3.3 g, 0.008 mol) was dissolved in 340 ml of THF. The solution of potassium tert-butoxide (34.2 g, 305 mol) in 340 ml of THF was prepared keeping the reaction flask in an icebath. The reaction mixture was stirred at 0° C. for 15 min and then 3.5 ml of water was added. The reaction mixture was stirred at room temperature for 10 min and the polymer solution was added to it slowly over a period of 30 min. The reaction mixture was stirred at room temperature for 96 hours and then poured into solution was heated to 65° C. for 3 hrs. The reaction mixture was filtered and acidified with 10% HCl. The precipitated product was washed with 2000 ml of water and dried overnight under vacuum. Additional purification was carried out using column chromatography and lyophilization of the eluant ammonium bicarbonate solution. The molecular weight averages of the product obtained from GPC using Multi Angle Laser Light Scattering Technique (dn/dc: 0.211 ml/g) were $8.932 \times 10^5$ for Mn and $1.258 \times 10^6$ for Mw.

We claim:

1. A composition for inducing an immunogenic response in an animal, comprising:

an antigen and a polyphosphazene polyelectrolyte adjuvant wherein at least a portion of said polyphosphazene polyelectrolyte has the formula:

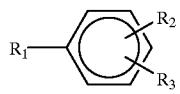

wherein each A is independently selected from X or Y in which (1) X is

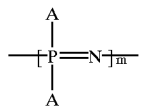

in which $R_1$ is —N($R_4$)—, —O— or —O$R_5$— where $R_4$ is hydrogen or a $C_1$–$C_4$ alkyl(preferably hydrogen) and $R_5$ is a $C_1$–$C_3$ alkylene(preferably methylene) moiety, $R_2$ is at least one carboxylic acid moiety which can be attached at any ring position directly or through an alkylene, preferably a methylene and $R_3$ is hydrogen or another substituent moiety such as an alkoxy, for example a methoxy moiety;

(2) Y is selected from the group consisting of
  (a) $(OCH_2CH_2)_nOR_6$ in which n is 1 to 120 and $R_6$ is a $C_1$ to $C_{10}$ hydrocarbon; and
  (b) (B)$OR_7$ in which B is a polyoxypropylene/polyoxyethylene block copolymer and $R_7$ is a $C_1$ to $C_{10}$ hydrocarbon, an aliphatic saturated or unsaturated hydrocarbon or an aromatic hydrocarbon, including alkyl substituted aromatic hydrocarbons;

(3) X and Y are in a range of ratios of 1:40 to 40:1; and (4) m is 3 to 100,000.

2. The composition of claim 1 wherein the polymer contains at least 10 percent or more of repeating units that are not susceptible to hydrolysis under the conditions of use.

3. The composition of claim 1 wherein the polyphosphazene polyelectrolyte is cross-linked with a multivalent cation.

4. The composition of claim 3 wherein the multivalent cation is selected from the group consisting of calcium, copper, aluminum, magnesium, strontium, barium, tin, zinc, iron, poly(amino acid), poly(ethyleneimine), poly(vinylamine) and polysaccharides.

5. The composition of claim 1 wherein the antigen is selected from the group consisting of protein, peptide, polysaccharide, glycoprotein, glycolipid, nucleic acid, or a combination thereof derived from a cell, bacteria, virus particle or a portion of any of them.

6. The composition of claim 1 wherein the polyphosphazene polyelectrolyte is covalently conjugated with an antigen.

7. The composition of claim 1 wherein X is selected from the group consisting of:

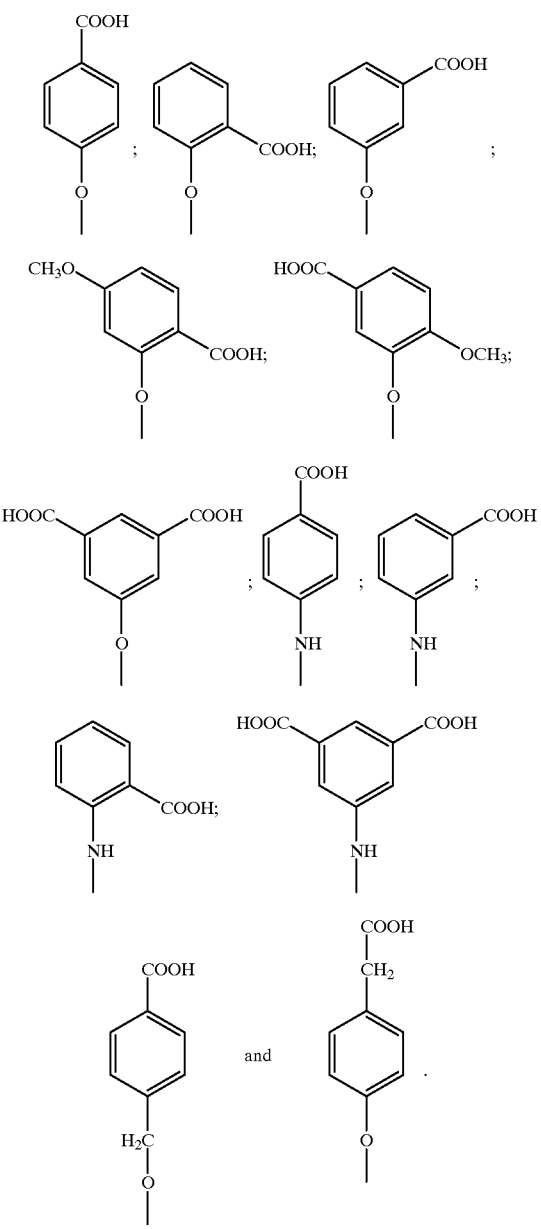

8. A method of inducing an immune response in an animal comprising the steps of administering to the animal an antigen and a polyphosphazene polyelectrolyte immunoadjuvant, wherein at least a portion of said polyphosphazene polyelectrolyte has the formula:

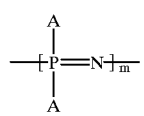

wherein each A is independently selected from X or Y in which (1) X is

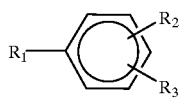

in which $R_1$ is —N($R_4$)—, —O— or —$OR_5$— where $R_4$ is hydrogen or a $C_4$–$C_4$ alkyl(preferably hydrogen) and $R_5$ $C_1$–$C_3$ alkylene (preferably methylene) moiety, $R_2$ is at least one carboxylic acid moiety which can be attached at any ring position directly or through an alkylene, preferably a methylene and $R_3$ is hydrogen or another substituent moiety such as an alkoxy, for example a methoxy moiety;

(2) Y is selected from the group consisting of
   (a) $(OCH_2CH_2)_nOR_6$ in which n is 1 to 120 and $R_6$ is a $C_1$ to $C_{10}$ hydrocarbon; and
   (b) $(B)OR_7$ in which B is a polyoxypropylene/polyoxyethylene block copolymer and $R_7$ is a $C_1$ to $C_{10}$ hydrocarbon, an aliphatic saturated or unsaturated hydrocarbon or an aromatic hydrocarbon, including alkyl substituted aromatic hydrocarbons;

(3) X and Y are in a range of ratios of 1:40 to 40:1; and (4) m is 3 to 100,000.

9. The method of claim 8 wherein the antigen is conjugated with the polyphosphazene polyelectrolyte.

10. The method of claim 8 wherein the antigen and polyphosphazene are administered separately to proximate sites.

11. The method of claim 8 wherein the antigen and polyphosphazene are first combined and the combination is administered to the animal.

12. The method of claim 8 wherein the method of administration is parenteral.

13. The method of claim 8 wherein the method of administration is oral.

14. A polyphosphazene polyelectrolyte adjuvant wherein at least a portion of said polyphosphazene polyelectrolyte has the formula:

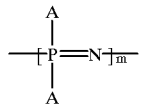

wherein each A is independently selected from X or Y in which
(1) X is

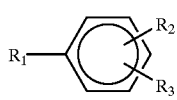

in which $R_1$ is —N($R_4$)—, —O— or —$OR_5$— where $R_4$ is hydrogen or a $C_1$–$C_4$ alkyl(preferably hydrogen) and $R_5$ is a $C_1$–$C_3$ alkylene(preferably methylene) moiety, $R_2$ is at least one carboxylic acid moiety which can be attached at any ring position directly or through an alkylene, preferably a methylene and $R_3$ is hydrogen or another substituent moiety such as an alkoxy, for example a methoxy moiety;

(2) Y is selected from the group consisting of
   (a) $(OCH_2CH_2)_nOR_6$ in which n is 1 to 120 and $R_6$ is a $C_1$ to $C_{10}$ hydrocarbon; and
   (b) $(B)OR_7$ in which B is a polyoxypropylene/polyoxyethylene block copolymer and $R_7$ is a $C_1$ to $C_{10}$ hydrocarbon, an aliphatic saturated or unsaturated hydrocarbon or an aromatic hydrocarbon, including alkyl substituted aromatic hydrocarbons;

(3) X and Y are in a range of ratios of 1:40 to 40:1; and (4) m is 3 to 100,000.

15. The polyphosphazene polyelectrolyte of claim 14 wherein the polymer contains at least 10 percent or more of repeating units that are not susceptible to hydrolysis under the conditions of use.

16. The polyphosphazene polyelectrolyte of claim 14 wherein the polyphosphazene polyelectrolyte is cross-linked with a multivalent cation.

17. The polyphosphazene polyelectrolyte of claim 16 wherein the multivalent cation is selected from the group consisting of calcium, copper, aluminum, magnesium, strontium, barium, tin, zinc, iron, poly(amino acid), poly (ethyleneimine), poly(vinylamine) and polysaccharides.

18. The polyphosphazene polyelectrolyte of claim 14 wherein the antigen is selected from the group consisting of protein, peptide, polysaccharide, glycoprotein, glycolipid, nucleic acid, or a combination thereof derived from a cell, bacteria, virus particle or a portion of any of them.

19. The polyphosphazene polyelectrolyte of claim 14 wherein the polyphosphazene polyelectrolyte is covalently conjugated with an antigen.

20. The polyphosphazene polyelectrolyte of claim 14 wherein X is selected from the group consisting of:

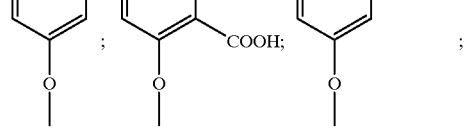

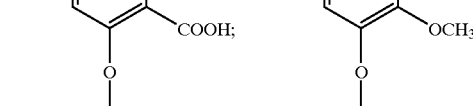

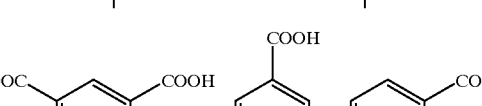

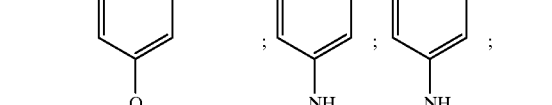

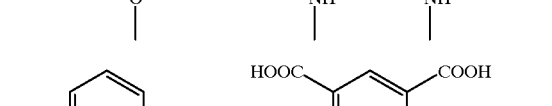

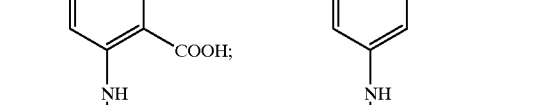

-continued

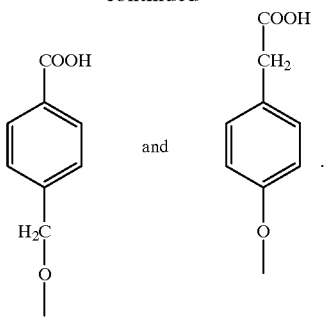
and

21. A polyphosphazene polyelectrolyte adjuvant wherein at least a portion of said polyphosphazene polyelectrolyte has the formula:

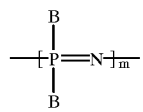

wherein each B is

Ortho-O—C$_6$H$_4$COOH.

22. A composition for inducing an immunogenic response in an animal, comprising:

an antigen and a polyphosphazene polyelectrolyte adjuvant wherein at least a portion of said polyphosphazene polyelectrolyte has the formula:

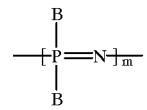

wherein m is 3 to 100,000 and each B is

Ortho-O—C$_6$H$_4$COOH.

* * * * *